US005643334A

United States Patent [19]
Eckhouse et al.

[11] Patent Number: 5,643,334
[45] Date of Patent: Jul. 1, 1997

[54] METHOD AND APPARATUS FOR THE DIAGNOSTIC AND COMPOSITE PULSED HEATING AND PHOTODYNAMIC THERAPY TREATMENT

[75] Inventors: Shimon Eckhouse; Michael Kreindel, both of Haifa, Israel

[73] Assignee: ESC Medical Systems Ltd., Yokneam, Italy

[21] Appl. No.: 385,190

[22] Filed: Feb. 7, 1995

[51] Int. Cl.⁶ .................................................. A61N 5/00
[52] U.S. Cl. ..................... 607/88; 607/89; 606/3; 606/13
[58] Field of Search ................. 607/88, 89; 606/3, 606/13

[56] References Cited

U.S. PATENT DOCUMENTS 5,344,434  9/1994  Talmore .

OTHER PUBLICATIONS

Medline Abstract 95003930 May 1994.
Medline Abstract 94324791 May 1994.

*Primary Examiner*—Paul J. Killos
*Attorney, Agent, or Firm*—Foley & Lardner

[57] ABSTRACT

The present invention is directed toward an apparatus and method for diagnostic and composite treatment of a wide range of solid tumors. More particularly, the invention relates to an efficient apparatus and method for diagnosing and simultaneously treating certain types of cancer with photodynamic therapy and pulse heating.

46 Claims, 5 Drawing Sheets

METHOD AND APPARATUS FOR THE DIAGNOSTIC AND COMPOSITE PULSED HEATING AND PHOTODYNAMIC THERAPY TREATMENT

BACKGROUND OF THE INVENTION

In general, the fundamental mechanism of photodynamic therapy (PDT) action is initiated by the absorption of visible light by a tumor that has been injected with a photosensitizing agent. As a result of the reaction of incident light in the range of 600 to 1000 nanometers (nm) with the photosensitizing agent, oxygen is generated in the singlet state. The reaction of this photochemically generated singlet oxygen with the intracellular lipids, proteins, and nucleotides harms the cancerous cells and ultimately results in tumor necrosis.

In the prior art, lasers and continuous wave (CW) non-coherent light sources were used for PDT. The delivery dose of the light energy varied in the range of 25 to 200 joules per square centimeter ($J/cm^2$) with a fluency rate of 10 to 200 milliwatts per square centimeter ($mW/cm^2$), depending upon the tumor size and the spectrum of the radiation.

Typically, the light source used for clinical PDT of solid tumors is a CW tunable dye laser that is pumped by an argon ion laser. Alternatively, a frequency doubled Nd:YAG pumped dye laser which produces pulsed light may be used.

As an alternative to laser light sources, CW wavelength filtered lamp sources may be used. For example, the use of a xenon short arc lamp of 150 W possessing a narrow light beam with a spectral region in the range of 610 to 750 nm is claimed in United States Patent No. 5,344,434, issued on Sept. 6, 1994, to Eli T. Talmore, entitled "Apparatus For The Photodynamic Therapy Treatment." A glass lens focuses the light beam to a range of 3 to 12 millimeters (mm) in diameter. The light beam is then delivered to the target through a light guide. To obtain the desired dose of radiation with this device, the treatment time preferably ranges from approximately 20 to 60 minutes, depending on the size of the tumor.

In the prior art, one cancer diagnostic method that is used is based on the fluorescence of malignant cells in the wavelength range of 400 to 750 nm under illumination of near ultraviolet (UV) and blue radiation in the range of 300 to 400 nm. The presence of malignant cells reduces the autofluorescent intensity in the blue green wavelength region, thus providing a signal that is distinguishable from the higher intensity signal originating from surrounding healthy tissue. Alternatively, diagnostic techniques may employ different types of injected photoactivators. Accumulation in the tumor of these alternate types of photoactivators results in increased fluorescence of the malignant cells in comparison to the surrounding healthy tissue.

Only a few types of light sources that can excite tissue autofluorescence are currently available. One example of such a light source is a nitrogen laser which emits 3 nanosecond (nsec) light pulses having a 337 nm wavelength. Another type of light source is a UV source, such as an excimer pumped dye laser, that produces a 308 nm light beam which is focused into a 600 micrometer (μm) thick optical fiber. As an alternative to the use of lasers as the exciting light source, mercury lamp sources which filter two excitation wavelengths of 365 and 405 nm may be employed.

There is, however, a need for a simple tunable apparatus and method for providing efficient PDT treatment for a wide range of tumor parameters, including size of the tumor and depth of location. Such an apparatus and method will preferably be able to control the fluency rate and spectrum of output radiation, dependent on the type of photosensitizing agent used, to achieve efficient PDT treatment. In addition, the apparatus and method preferably will produce radiation with the appropriate wavelength range desirable for cancer diagnostics. In addition, an apparatus and method using pulsed light rather than CW light would be advantageous because pulsed light enables better temperature control and the achievement of important hyperthermion effects.

SUMMARY OF THE PRESENT INVENTION

The present invention achieves efficient diagnosis and treatment of cancerous cells. The method and apparatus of the invention simultaneously provide photodynamic therapy and pulsed heating of the tumor, which accelerate the photochemical reaction and coagulate the blood, thus limiting the supply of blood to the tumor.

The apparatus of the present invention includes either a linear flashlamp in a housing with a straight reflector, or a bent flashlamp with a cone reflector, or any other light source suitable for the desired use. When used for diagnostic purposes, interchangeable interference filters provide a spectral region of 350 to 500 nm with a peak at 400 nm. The apparatus also includes an interchangeable filter which filters radiation with wavelengths shorter than 520 nm. Another interchangeable filter provides either a spectral region of 600 to 700 nm or a spectral region of above 600 nm. The produced light beam may be directed to the target through either a flexible light guide or a shorter quartz light guide, or directly from the output of the light source.

In the diagnostic mode, the invention can also be operated in either a pulsed or CW mode. In the pulsed mode a single pulse or repetitive pulses having a frequency of 0.02 to 2 pulses/sec may be used. Pulse duration may be varied over a range, for example from 0.1 to 100 msec. Optical energy density per pulse ranging from 0.02 to 4 $J/cm^2$ (in each pulse) and an illumination area that varies in size dependent upon the distance of the target area from the light guide may also be provided.

In the CW mode the suspected cancerous area is continuously illuminated while the physician looks for fluorescence that indicates the presence of a tumor. Illumination can be carried out through a light guide or by directly exposing the area to the opening in the housing that contains the lamp. The light guide is particularly useful for illuminating internal objects and areas that are difficult to access. When treating large surface areas, the light source may be used without the light guide.

Similarly, in the PDT treatment mode either pulses or a CW may be provided.

Pulses having a frequency ranging from 0.1 to 1 pulse/sec and durations of from 0.1 to 100 msec may be used. The ouput spectrum is preferably in the range of either 600 to 1000 nm or 600 to 700 nm. The light beam may be delivered to the target either directly or by a flexible light guide if internal treatment is desired and for external treatment of a large surface, the light beam can be delivered directly to the target without a light guide. An optical energy density per pulse ranging from 0.1 to 20 $J/cm^2$ (pulse) in repetitive mode is preferably provided as is a fluency rate ranging from 100 to 2000 $mW/cm^2$. The illumination area preferably varies from 0.5 to 3 $cm^2$.

In the CW treatment mode the treated object is continuously illuminated by the filtered lamp radiation. Illumination can be achieved either through a light guide or by directly exposing the treated area to the opening in the housing that contains the lamp. The light guide can be used for treating internal and small size tumors, and areas that are difficult to access. When treating large surface areas, the light source may be used without the light guide.

The apparatus and method of the invention can be used for photodynamic therapy treatment using a variety of different photosensitizers. The resulting irradiance from the invention is significantly higher than the radiation produced by the commonly used laser and noncoherent light sources. In addition, the invention permits treatment of large areas in a much shorter time than is possible with currently used methods. Also, the invention provides a further advantage in that it is very safe and poses minimal risk of accidental harm to the operator and the patient.

Other principal features and advantages of the invention will become apparent to those skilled in the art upon review of the following drawings, the detailed description, and the appended claims.

Before explaining at least one embodiment of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION OF THE PREFERRED EMBODIMENTS

Generally, in the present invention, tumor necrosis consists of a composite effect of three processes. The first process is photodynamic therapy whose mechanism is initiated with the absorption of light by a photosensitive agent which has a much higher accumulation effect in cancer cells than in normal cells. Due to a photochemical reaction of incident light in the range of 600 to 1000 nm with this photosensitive agent, oxygen is generated in the singlet state. The reaction of this photochemically generated singlet oxygen with intracellular lipids, proteins, and nucleotides is deleterious to the cells and ultimately results in tumor necrosis.

The second process is pulsed heating of the tissue. The photochemical reaction of incident light with a photosensitive agent can be accelerated by heating tissue to a temperature which is significantly higher than normal temperature but lower than the temperature at which proteins coagulate. The absorption coefficient of skin or other tissue significantly depends upon the type of skin. Consequently, the spectrum of incident radiation and the power of light pulses is preferably varied over a wide range. The absorption coefficient of tissue is a function of light wavelength. Thus, for light in the radiation range of 600 to 700 nm, the depth of penetration into the dermis ranges up to approximately 1 mm. As a result, this range of radiation can be used to heat only a shallow surface layer of tissue or skin. Radiation having a wavelength range of 700 to 1200 nm can penetrate the dermis more deeply. Thus, tissue as deep as approximately 3 mm may be heated using such radiation. Because the epidermis absorption coefficient is significantly higher than that of the dermis, however, care should be taken to avoid overheating the epidermis. Transparent gel applied to the surface of the skin can prevent overheating.

The cooling time (t) of an object that has typical dimension (d) and diffusivity (a) can be written as:

$$t = d^2/a$$

Typically, the epidermis has cross dimensions of less than 0.1 mm. The diffusivity (a) is approximately $3 \times 10^{-7}$ $m^2 sec^1$. Thus, when gel is applied to the skin, the typical cooling time of the epidermis will be approximately 33 msec. Gel application allows the epidermis to cool during the pulse delay and thus avoids adverse heating effects.

The third process used for tumor necrosis is to limit the blood supply to the tumor by coagulating the blood which results in lesion of the vessels surrounding the tumor. The absorption coefficient of blood is much higher than that of dermis or tissue for radiation in the wavelength range of 600 to 1000 nm. Hence at optimal chosen parameters of incident radiation, blood coagulation is possible without damaging the dermis and epidermis.

The composite effect of these three processes results in a more efficient necrosis of cancer cells. This combination decreases treatment time to approximately 5 minutes while simultaneously increasing the cancer necrosis effect.

Figure 1:
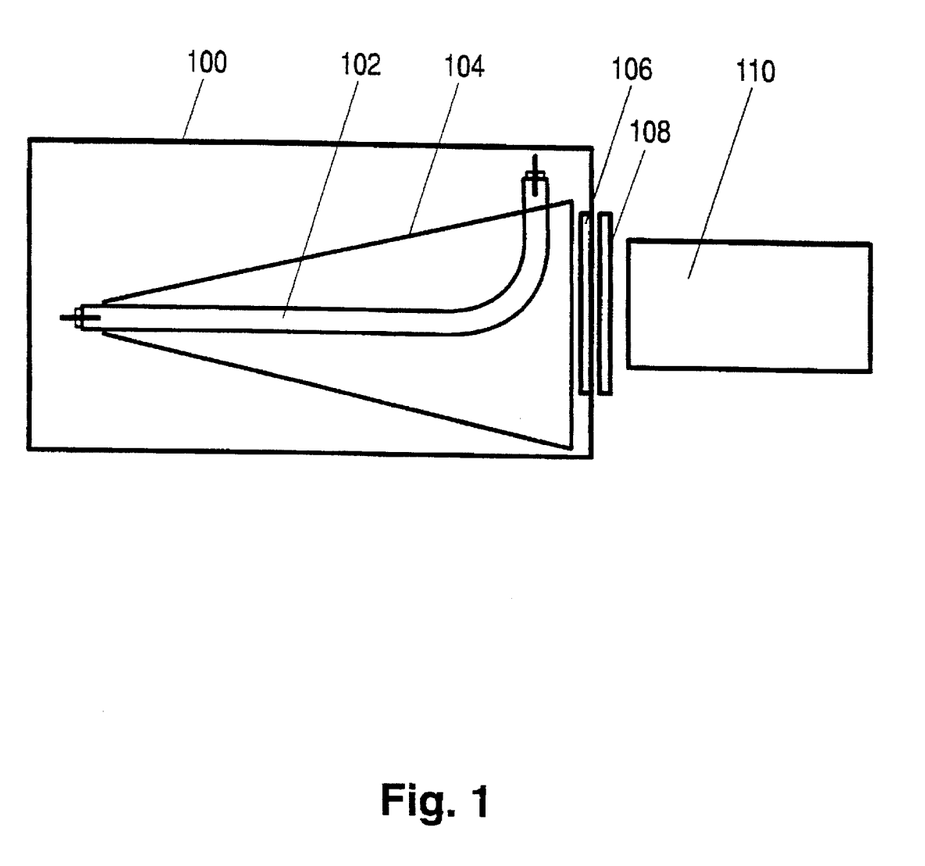
FIG. 1 is a schematic illustration of the apparatus according to a preferred exemplary embodiment of the present invention having a bent lamp and a cone reflector.

Referring now to FIG. 1, an operating head 100 encases a bent flashlamp 102, a silver coated conical reflector 104, and interchangeable interference filters 106. Filters 106 cut off the radiation spectrum at 520 nm. Transmission of radiation through filter 106 is dependent upon the incident angle of the radiation. Filter 106 reflects (does not transmit) any nonuseful incident radiation, thus avoiding overheating an absorbing filter 108.

Absorbing filter 108 and light guide 110 are external to operating head 100. Filter 108 cuts off radiation at 600 nm. Transmission through filter 108 of radiation having a wavelength less than 580 nm is less than $10^{-5}$. Light guide 110 may be either a flexible light guide or a quartz light guide.

Flashlamp 102 may be operated in either CW mode or pulse repetitive mode. Reflector 104 focuses the light beam produced by flashlamp 102 and conducts the beam through interference filter 106 and absorbing filter 108 to light guide 110. Light guide 110 guides the light beam to treatment areas that are difficult to access, small targets, and internal tumors. Alternatively, light guide 110 may be decoupled from operating head 100. In such a configuration, the light beam produced by operating head 100 can be directly used to treat large, external tumors.

Figure 2:
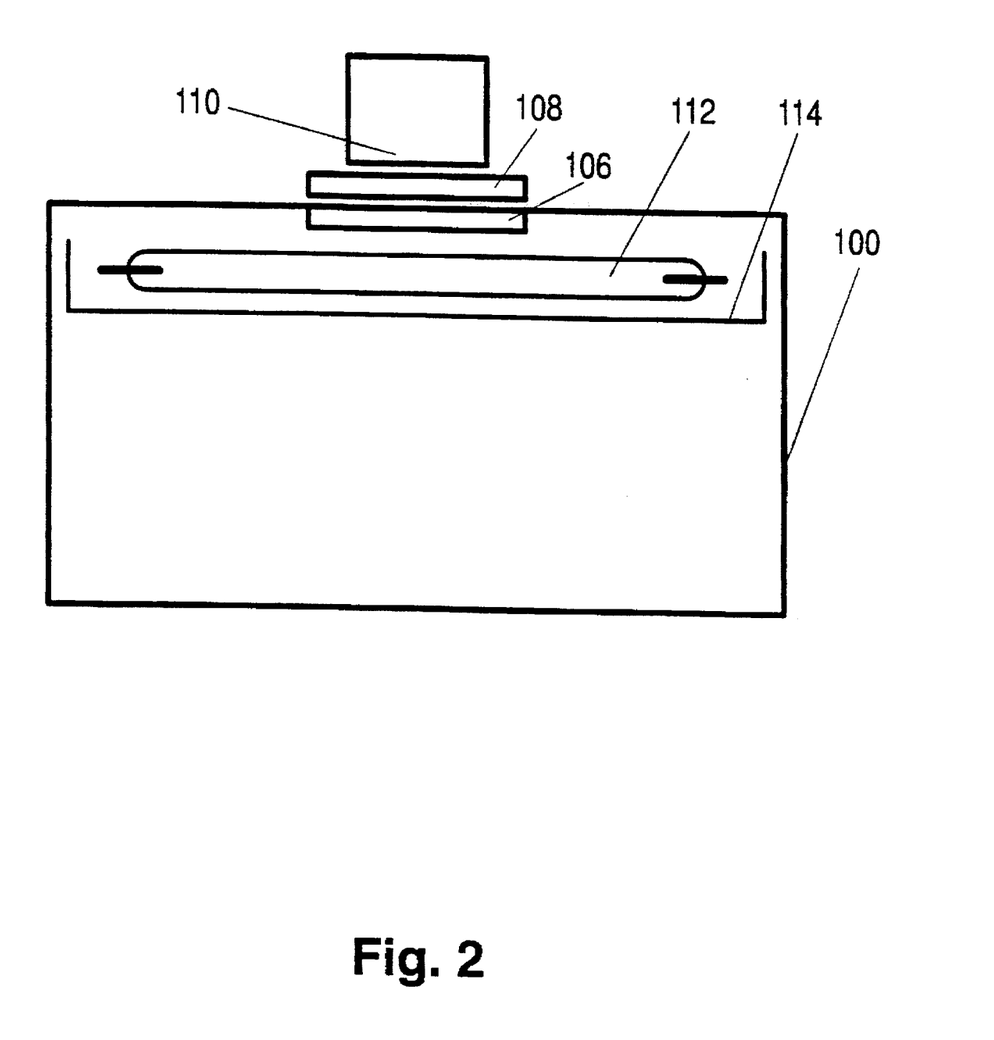
FIG. 2 is a schematic illustration of the apparatus according to another preferred exemplary embodiment of the present invention having a linear flashlamp and a straight reflector.

Referring now to FIG. 2, an alternative exemplary embodiment of the invention is shown. Rather than using a bent flashlamp and conical reflector, this alternative embodiment employs a linear flashlamp 112 with a straight reflector 114.

When operating in the pulse mode, the invention produces a train of pulses at a repetition rate that varies from 0.1 to 10 pulses/second. The total number of pulses per pulse train can be selected in the range of 1 to 1000. The total dose to the treated area is the product of the number of pulses and the fluency per pulse.

Figure 3:
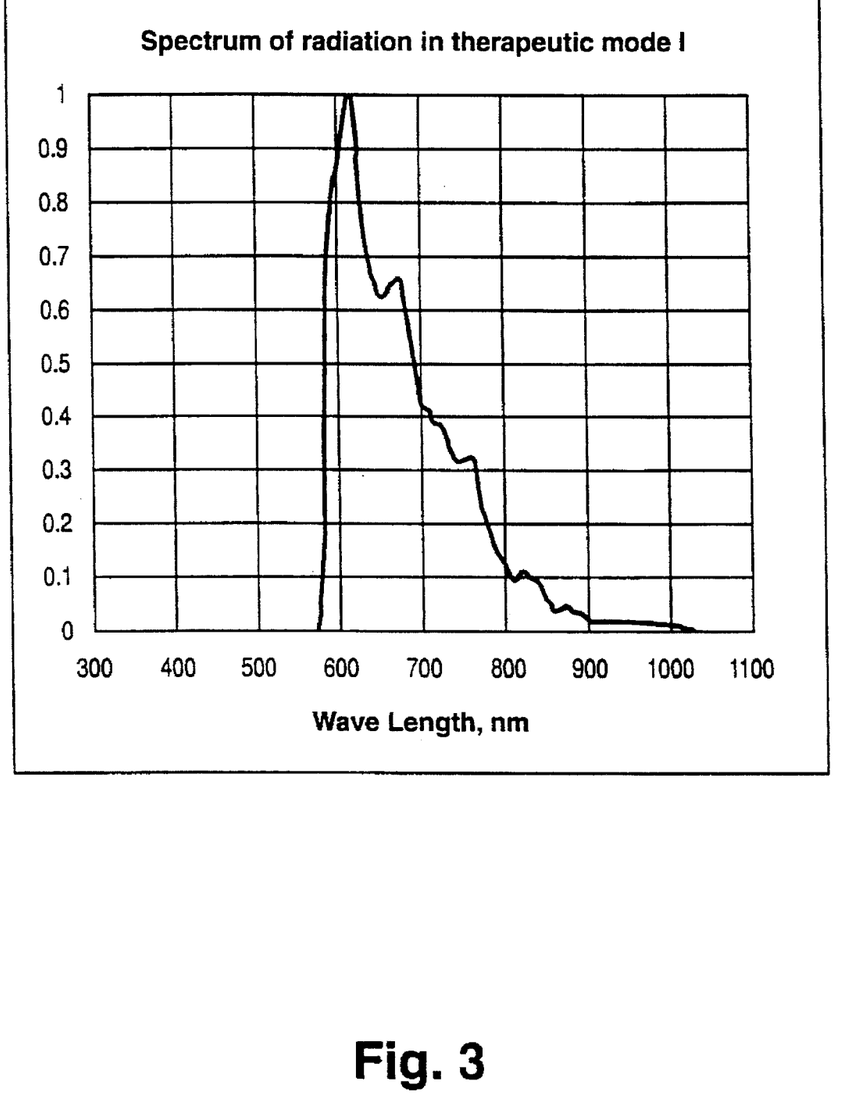
FIG. 3 is a typical normalized output radiation spectrum in treatment mode with heating.

In the therapeutic mode, two different spectral distributions can be selected. Referring now to FIG. 3, the spectral distribution peaks at 615 nm and has a tail that reaches up to 1000 nm in therapeutic mode I. In addition, the spectral distribution of the radiation can be controlled by varying the pulse parameters. For example, if it is necessary to increase the heating effect at a deeper depth, the long wavelength part of the radiation should be increased by decreasing the pulse power.

Figure 4:
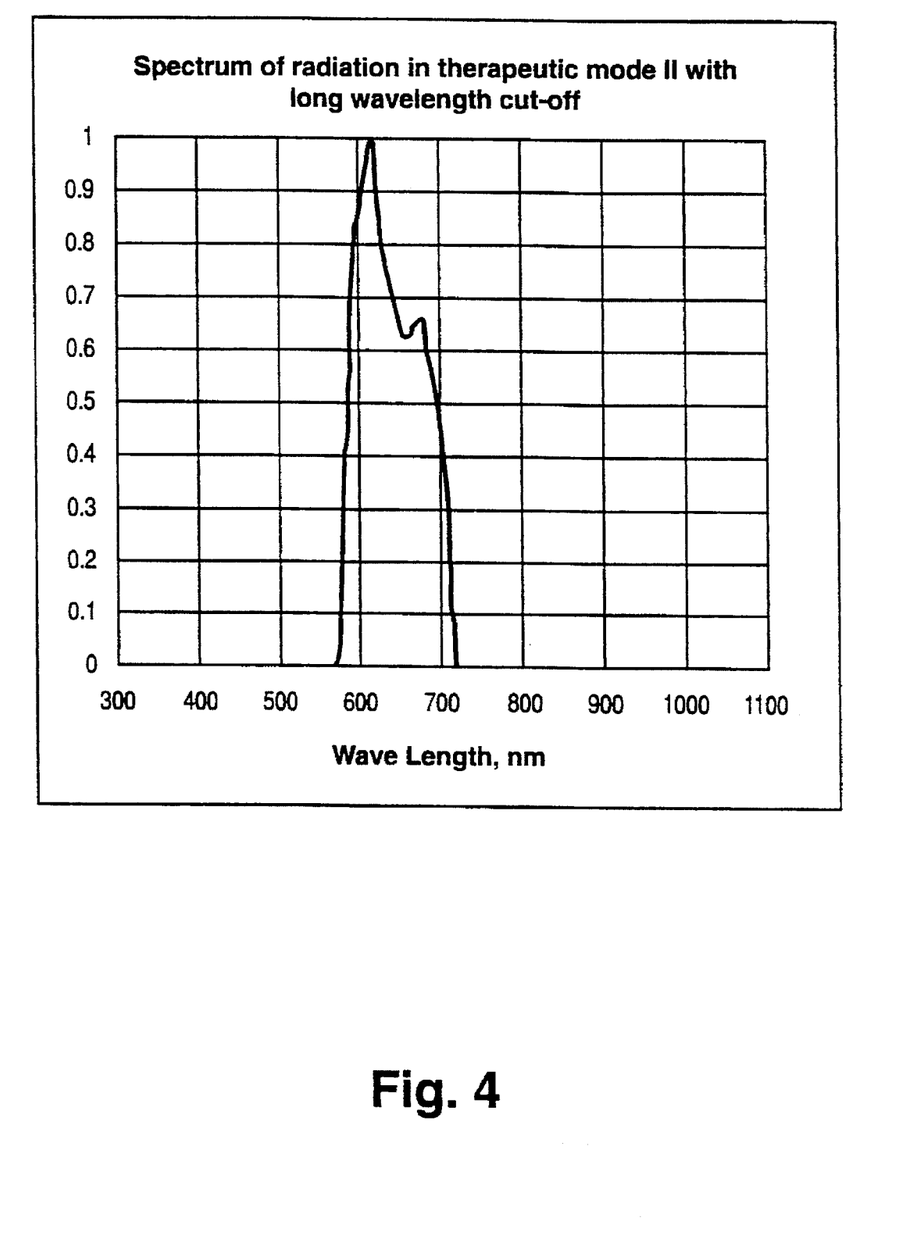
FIG. 4 is a typical normalized output radiation spectrum in treatment mode with long wavelength cut off.

Referring now to FIG. 4, in therapeutic mode II the spectrum of the radiation is cut off at 700 nm by an interference filter which is installed in place of absorbing filter 108. Due to this filter, no significant radiation is emitted having a wavelength greater than approximately 700 nm. Mode II can be used if minimum heating of tissue is desired.

The fluency generated in the therapeutic mode is a function of the distance between the face of light guide 110 and the treatment area. The operator can input this distance and the device calculates the fluency per pulse and the total dose corresponding to the selected distance.

The pulse duration can be varied in the range of 0.1 to 100 msec and the energy per pulse is variable in the range of 0.1 to 10 J/cm$^2$ (the 10 J/cm$^2$ is generated on the face of the light guide).

In the CW mode, the output radiation power density can be varied up to 1000 mW/cm$^2$. Heating effects are not a concern in this operating mode because the heating of the tumor and surrounding blood vessels is compensated by cooling due to the heat conductivity process.

For diagnostic purposes, both the CW mode and multiple pulse trains with a repetition rate of 0.01 to 0.2 pulse/sec may be used. The invention provides the necessary total light energy per pulse with radiation in the range of 350 to 500 nm with a variable pulse duration of 1 to 10 ms. The illuminated area may be as large as desired.

Figure 5:
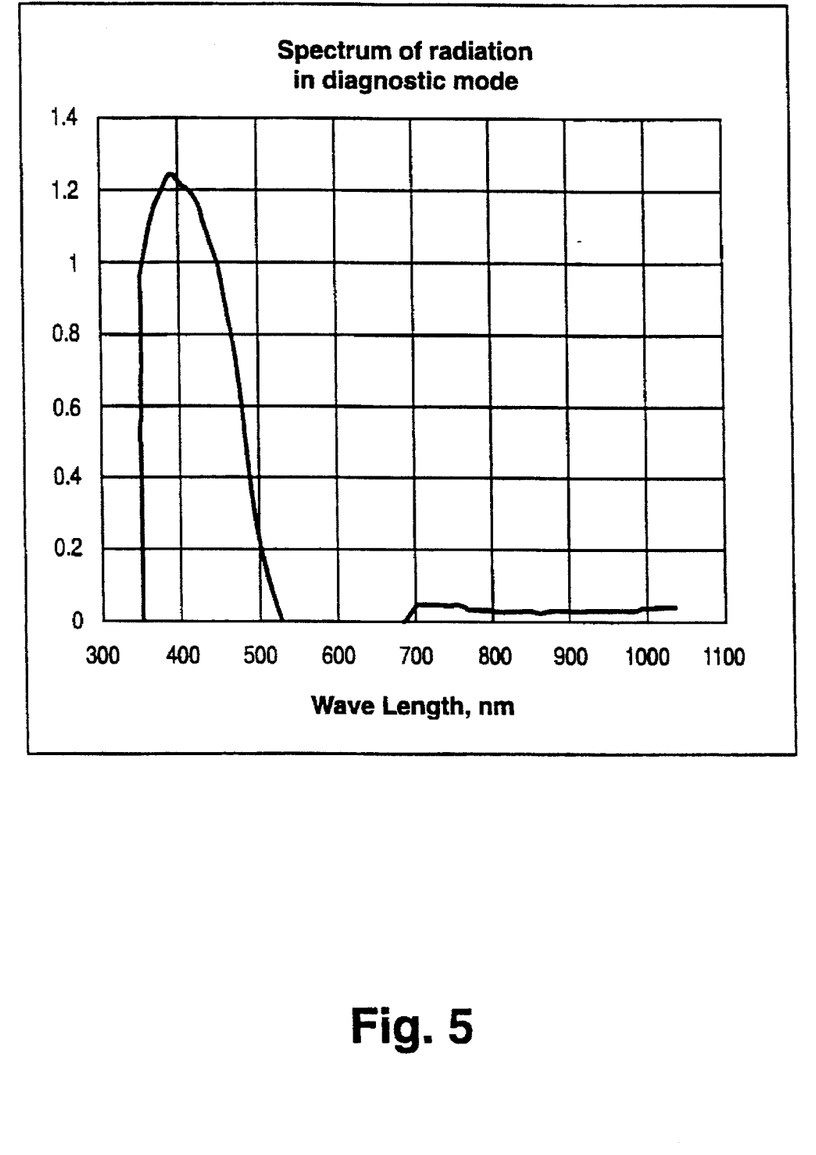
FIG. 5 is a typical normalized output radiation spectrum in diagnostic mode.

FIG. 5 represents the normalized spectrum of radiation. As shown, the maximum level of radiation is at 400 nm. The necessary energy and power density may be obtained by varying the pulse repetition rate and energy per pulse. The exposed area can be modified by varying the distance from light guide 110 to the target. In the CW mode, the fluency rate can be as large as dozens of watts per square centimeter. For treatment of large areas, the light beam can be delivered directly to the target without light guide 110.

Operating parameters have been given above and are restated below, with alternatives. The operating parameters are exemplary and are not intended to be limiting.

In the diagnostic mode, the invention provides an output radiation including the following parameters:

(1) either single pulse or repetitive pulse modes of operation with a frequency of 0.02 to 2 pulses/sec;

(2) pulse duration that may be varied from 0.1 to 100 msec;

(3) a spectrum of radiation in the range of 350 to 500 nm with a peak at 400 nm;

(4) delivery of the light beam to the target area by either a quartz or a flexible light guide;

(5) optical energy density per pulse ranging from 0.02 to 4 J/cm$^2$ (in each pulse); and (6) an illumination area that varies in size dependent upon the distance of the target area from the light guide.

In the diagnostic mode, the invention can also be operated in CW mode, in which the suspected cancerous area is continuously illuminated while the physician looks for fluorescence that indicates the presence of a tumor. Illumination can be carried out through a light guide or by directly exposing the area to the opening in the housing that contains the lamp. The light guide is particularly useful for illuminating internal objects and areas that are difficult to access. When treating large surface areas, the light source may be used without the light guide.

In the PDT treatment mode, the invention provides the following output parameters:

(1) continuous operation mode or repetitive mode with a frequency ranging from 0.1 to 1 pulse/sec;

(2) pulse duration that may be varied from 0.1 to 100 msec;

(3) spectrum of radiation in the range of either 600 to 1000 nm or 600 to 700 nm;

(4) delivery of the light beam to the target either directly or by a flexible light guide if internal treatment is desired;

(5) for external treatment of a large surface, the light beam can be delivered directly to the target without a light guide;

(6) optical energy density per pulse ranging from 0.1 to 20 J/cm$^2$ (pulse) in repetitive mode;

(7) fluency rate ranging from 100 to 2000 mW/cm$^2$; and (8) illumination area that varies from 0.5 to 3 cm$^2$.

Thus, it should be apparent that there has been provided in accordance with the present invention a method and apparatus for the diagnostic and composite pulsed heating and photodynamic therapy treatment that fully satisfy the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

The embodiments of the invention in which an exclusive property or privilege is claimed are defined as follows:

1. A composite method of cancer cells necrosis, comprising:

pulsed photodynamic therapy treatment;

pulsed heating of tissue for acceleration of photochemical reaction; and treatment of vessels with noncoherent light in the tumor to limit blood supply of a tumor.

2. A method of using transparent gel in photodynamic therapy in order to cool down epidermis and avoid its overheating.

3. A method for therapeutically treating cancerous cells within a tissue having a plurality of vessels for supplying blood thereto, comprising the steps of:

providing a pulsed, noncoherent light beam;
treating the cancerous cells with a photosensitive agent; and
directing the light beam to the tissue, and to the plurality of vessels surrounding the cancerous cells limiting blood supply to the cancerous cells.

4. The method of claim 3 further including the step of filtering the noncoherent light beam to provide a filtered light beam having a range of wavelengths.

5. The method of claim 3 further including the step of directing the light beam to the cells treated with the photosensitive agent to generate oxygen in a singlet state.

6. The method of claim 3 wherein the step of treating includes the step of treating the tissue with a photosensitive agent having a higher accumulation effect in cancerous cells than in normal cells.

7. The method of claim 3 further comprising the step of applying transparent gel to an epidermis to prevent overheating of the epidermis.

8. The method of claim 3 wherein the step of directing the light beam includes the step of guiding the light beam to the tissue with a light guide.

9. A method for providing therapeutic treatment of cancerous cells within a tissue having a plurality of vessels for supplying blood thereto, comprising the steps of:
providing a source of light;
treating the tissue with a photosensitive agent having a higher accumulation effect in cancerous cells than in normal cells;
directing the light to the tissue treated with the photosensitive agent to generate oxygen in a singlet state;
heating the tissue with the light to accelerate treatment; and
directing the light to the plurality of vessels surrounding the cancerous cells to limit blood supply to the cancerous cells.

10. The method of claim 9 wherein the step of providing a source of light includes the step of providing a source on noncoherent light.

11. The method of claim 9 further including the step of filtering the light to provide light having a range of wavelengths.

12. The method of claim 9 wherein the step of providing includes the step of providing a pulsed light beam.

13. The method of claim 12 wherein the step of providing a pulsed light beam includes the step of providing a selectable pulse duration, a selectable pulse frequency, and a selectable energy density per pulse.

14. The method of claim 9 further including the step of applying transparent gel to an epidermis to prevent overheating of the epidermis.

15. The method of claim 9 wherein the step of providing includes the step of providing a continuous wave light beam having a selectable variable power density.

16. The method of claim 9 wherein the step of directing includes the step of guiding the filtered light beam to the tissue with a light guide.

17. An apparatus for therapeutically treating cancerous cells within a tissue having a plurality of vessels for supplying blood thereto, comprising:
a housing, including a window through which light can pass;
a pulsed, noncoherent source of light disposed in the housing; and
a reflector, disposed in the housing, that directs the light through the window, wherein the light is used for photodynamic therapy and to heat the blood vessels supplying blood to the tumor, thereby limiting the supply of blood to the tumor.

18. The apparatus of claim 17 further including a filter disposed in a path of the light to provide a filtered light beam having a range of wavelengths.

19. The apparatus of claim 17 further including a light guide having a proximal end disposed near the window and a distal end capable of being disposed near the tissue.

20. The apparatus of claim 18 wherein the light guide is a flexible light guide.

21. The apparatus of claim 18 wherein the light guide is a quartz light guide.

22. The apparatus of claim 17 wherein the light source may be operated in a continuous or pulsed mode.

23. An apparatus for diagnosing and therapeutically treating cancerous cells within a tissue having a plurality of vessels for supplying blood thereto, comprising:
a housing, including a window through which light can pass;
a source of light, capable of being operated in both a continuous mode and a pulsed mode, disposed in the housing; and
a reflector, disposed in the housing, that directs the light through the window.

24. The apparatus of claim 23 further including a filter disposed in a path of the light to provide a filtered light beam having a range of wavelengths.

25. The apparatus of claim 23 further including a light guide having a proximal end disposed near the window and a distal end capable of being disposed near the tissue.

26. The apparatus of claim 25 wherein the light guide is a flexible light guide.

27. The apparatus of claim 25 wherein the light guide is a quartz light guide.

28. The apparatus of claim 23 wherein the light source is a noncoherent source.

29. A method for diagnosing cancerous cells within a tissue, comprising the steps of:
directing light to the tissue;
treating the tissue with a photosensitive agent having a higher accumulation effect in cancerous cells than in normal cells; and
illuminating the tissue with the filtered light beam to provide a visual indication of cancerous cells.

30. The method of claim 29 further including the step of filtering the light beam to provide a filtered light beam having a range of wavelengths.

31. The method of claim 29 wherein the step of directing includes the step of generating noncoherent light.

32. The method of claim 29 wherein the step of directing includes the step of generating a pulse of light having a selectable pulse duration and selectable energy density.

33. The method of claim 29 wherein the step of directing includes the step of generating pulsed light having a selectable frequency.

34. The method of claim 29 wherein the step of directing includes the step of generating a continuous wave of light having a selectable power density.

35. The method of claim 29 wherein the step of directing includes the step of guiding the filtered light beam to the tissue with a light guide.

36. An apparatus for the therapeutic treatment and diagnosis of cancerous cells within a tissue, comprising:
a light source;
a filter system disposed in a path of the light to limit the light to a range of wavelengths; and a reflector to focus the light beam and to conduct the light beam through the filter system, wherein the light is used for photodynamic therapy and to heat the blood vessels supplying blood to the tumor, thereby limiting the supply of blood to the tumor.

37. The apparatus of claim 36 further including a light guide disposed to guide the filtered light to the tissue.

38. The apparatus of claim 37 wherein the light guide is a flexible light guide.

39. The apparatus of claim 37 wherein the light guide is a quartz light guide.

40. The apparatus of claim 39 wherein the light source is a source of noncoherent light.

41. The apparatus of claim 40 wherein the light source is a source of pulsed light.

42. The apparatus of claim 41 wherein the light source is capable of providing a selectable pulse frequency, a selectable pulse duration, and a selectable energy density per pulse, and further wherein the number of pulses may be varied.

43. The apparatus of claim 36 wherein the light source is a source of continuous wave having a selectable power density.

44. The apparatus of claim 36 wherein the filter system includes a first interference filter and an absorbing filter.

45. The apparatus of claim 17 wherein the light source is a linear flashlamp and the reflector is a straight reflector.

46. The apparatus of claim 17 wherein the light source is a bent flashlamp and the reflector is a conical reflector.

* * * * *